United States Patent [19]
Hemling et al.

[11] Patent Number: 6,030,633
[45] Date of Patent: Feb. 29, 2000

[54] FILM-FORMING COMPOSITIONS FOR PROTECTING ANIMAL SKIN

[75] Inventors: Thomas C. Hemling, Lake Winnebago, Mo.; Mark A. Henderson, Lenxa, Kans.; Chris B. Stapley, Platte City, Mo.

[73] Assignee: West Agro, Inc., Kansas City, Mo.

[21] Appl. No.: 09/080,509

[22] Filed: May 18, 1998

[51] Int. Cl.[7] .................................................. A01N 28/10
[52] U.S. Cl. ...................... 424/407; 424/78.07; 424/401; 424/406; 424/438; 424/488; 424/409
[58] Field of Search ................................ 424/78.07, 401, 424/406, 407, 438, 488, 409

[56] References Cited

U.S. PATENT DOCUMENTS

| | | |
|---|---|---|
| 4,156,067 | 5/1979 | Gould . |
| 4,584,192 | 4/1986 | Dell et al. . |
| 5,192,536 | 3/1993 | Huprich . |
| 5,413,780 | 5/1995 | Huprich . |
| 5,688,498 | 11/1997 | Huprich et al. . |

FOREIGN PATENT DOCUMENTS

| | | |
|---|---|---|
| 426486 | 8/1991 | European Pat. Off. . |
| 2737114 | 1/1997 | France . |
| 56115703 | 9/1993 | Japan . |
| 9617615 | 6/1996 | WIPO . |

OTHER PUBLICATIONS

Masashige Morikane;Abstract of Publication 56–55311; *Embrocation for Forming Film* Published, May 15, 1981.

*Primary Examiner*—Neil S. Levy
*Attorney, Agent, or Firm*—Hovey, Williams, Timmons & Collins

[57] ABSTRACT

Improved film-forming skin protectant compositions are provided which are capable of forming a long-lasting elastic barrier film when applied to skin; the compositions have particular utility as barrier teat dips, for protecting cows against mastitis, especially during their susceptible non-lactating periods. The compositions include a film-forming component (preferably a mixture of polyether polyurethane and benzoin gum) dispersed in a compatible carrier and further having a minor amount of nitrocellulose incorporated therein in order to increase the time of adherence of the composition to skin, as compared with an otherwise identical composition without nitrocellulose. The compositions may also include a germicide (e.g., chlorhexidine diacetate), and a coloring dye. The most preferred compositions include polyether polyurethane, benzoin gum, a solvent system made up of tetrahydrafuran and a lower alcohol, and chlorhexidine diacetate.

27 Claims, No Drawings

FILM-FORMING COMPOSITIONS FOR PROTECTING ANIMAL SKIN

BACKGROUND OF THE INVENTION

1. Field of the Invention

The present invention is concerned with improved film-forming skin protectant compositions capable of forming an elastic film when applied to skin and including a film-forming component dispersed in a carrier, and wherein the compositions of the invention are improved by provision of a quantity of nitrocellulose dispersed in the carrier; the nitrocellulose serves to create a more long-lasting film capable of protecting skin (e.g., the skin of bovine teats) over relatively long periods of time. More particularly, the preferred forms of the invention pertain to film-forming compositions including therein effective amounts of polyether polyurethane and benzoin gum dispersed in tetrahydrafuran (THF) solvent, with a minor amount of nitrocellulose therein.

2. Description of the Prior Art

A significant problem for dairy farmers is the incidence of mastitis in cattle. It is known that up to 40–50% of inflammatory infections are contracted to a cow's dry or non-lactating period, with the greatest percentages of these infections occurring the first and last two weeks of the dry period. At these times, the mammary gland is in the transitional state where immunological factors are preoccupied or suppressed, milk is no longer being flushed from the gland, and increased mammary pressure distends the teat, thus allowing for easier bacterial penetration through the milk canal.

It is known to apply protective compositions to bovine teats, especially during or leading up to the non-lactating period, in order to minimize the occurrence of mastitis. The primary goal in such mastitis treatment is to minimize bacterial exposure on the teat ends.

U.S. Pat. No. 5,192,536 describes protectant compositions containing polyether polyurethane dissolved in tetrahydrafuran. The compositions of this patent can be applied to animal skin to form a rapidly drying, elastic film having protectant qualities. U.S. Pat. No. 5,688,498 describes further compositions of this general character, but which are improved by the provision of benzoin gum (benzoin resinoid). It has been found that the benzoin gum significantly increases the adhesion time of the protectant compositions and renders the compositions suitable for dipping so as to improve the coverage of the compositions and for ease of use.

Pending application for U.S. Letters Patent Ser. No. 08/644,009, filed Feb. 14, 1997 is related to the '498 patent and describes further compositions making use of a variety of different solvents and additional ingredients such as germicides, dyes and optional ingredients, e.g., fillers, moisturizers, perfumes, and viscosity modifiers.

In addition to mastitis control, skin-protectant compositions also find utility as wound dressings to be applied to open wounds to protect against infection from dirt, insects or other sources of bacteria.

In order to enhance the protectiveness of skin protectant compositions of the forgoing types, it is desirable that it should remain intact on skin for as long as possible. This not only provides an added measure of protection against infection, but also lessens the time and expense involved in repeated reapplications of the compositions.

There is accordingly a need in the art for improved skin-protectant compositions which maintain the ease of use and protection capabilities of the known polyether polyurethane/benzoin gum compositions while giving increased wear integrity and longevity.

SUMMARY OF THE INVENTION

The present invention overcomes the problems outlined above, and provides greatly improved skin protectant compositions capable of forming an elastic film when applied to skin; such compositions broadly include a film-forming component dispersed in a carrier wherein the improvement of the invention comprises the addition of a quantity of nitrocellulose dispersed in the carrier in an amount sufficient to increase the time of adherence of the compositions to the skin, as compared with an otherwise identical composition which does not include the nitrocellulose.

In preferred forms, the nitrocellulose is present at a level of from about 0.2–15% by weight in the film-forming protectant compositions of the invention, and more preferably at a level of from about 1–10% by weight, and most preferably about 1.5–5% by weight. Nitrocellulose is available commercially in several grades that vary in the degree of polymerization and nitration. Essentially all such commercially available nitrocellulose products are useful in the context of the present invention, although amounts of use for respective grades may vary.

The preferred film-forming component of the present invention is made up of a mixture of polyether polyurethane and benzoin gum. The overall film-forming component is preferably present at a level of from about 5–50% by weight, and more preferably from about 7–25% by weight in the compositions of the invention. In more detail, the polyether polyurethane is normally used at a level of from about 5–25% by weight, more preferably from about 5–15% by weight; on the other hand, the benzoin gum is normally present at a level of from about 2–20% by weight, and more preferably at a level of from about 2–10% by weight. The carrier portion of the compositions is preferably a solvent for the film-forming component. The most preferred solvent is a mixture of tetrahydrafuran and alcohol, with the latter component being present at a level of from about 0.1–30% by weight, and more preferably at a level of from about 5–25% by weight. In addition to the foregoing though, a wide variety of other solvents can be used so long as the overall composition is stable at ambient temperature and has a sufficiently rapid drying time on the skin (preferably up to about 20 minutes, and more preferably up to about 10 minutes following skin application). Suitable solvents can therefore be selected from the group consisting of THF, cyclohexanone, toluene, acetone, the alkylene glycols (e.g., propylene or ethylene glycol) and the $C_1$–$C_4$ ethers, ketones and alcohols (trimethylether, diethylether, methylethylether, acetone, methylethylketone, diethylketone, methanol, ethanol, propanol, isopropanol or butanol).

The compositions of the invention may also have a germicidal agent dispersed in the carrier, which is normally used at a level of from about 0.01–2% by weight, and more preferably at a level of from about 0.05–1% by weight. The germicidal agent may be selected from a wide variety of effective agents, such as those taken from the group consisting of the linear or branched chain fatty acids (octanoic acid, nonanoic acid, decanoic acid), sodium pyridinathione, polyhexamethylene, biguanide, chlorhexidine diacetate and quaternary ammonium compounds such as the salts of alkyl dimethyl-benzyl ammonium, dialkyl dimethyl ammonium compounds and benzthonium. Combinations of such germicides may also be used, so long as the germicides themselves, and in combination with the other ingredients, form compatible compositions which are physically and chemically stable at ambient temperatures.

Dyes may also be added to the skin protectant compositions of the invention in order to improve the visualization of the barrier film on the skin area being treated. Acceptable dyes include those that are soluble or dispersible in the liquid compositions of the invention. The preferred dyes provide easy visualization of the barrier film from a distance of at least 20 feet and can be used at relatively low concentrations. Dyes should be used at a level of from about 0.001–0.5% by weight in the compositions, and more preferably at a level of from about 0.005–0.2% by weight. Dyes are normally selected from the group consisting of the D&C red 19, solvent yellow 43, fluoro yellow napthalic acid amide, Keyplast yellow TGH, FD&C red 3, FD&C red 22, FD&C red 28, FD&C red 39, FD&C red 19, FD&C green 6, orange 5, orange 10, orange 17, red 17, red 21, red 27, red 31, violet 2, yellow 7 and yellow 11.

In order to be most useful the compositions of the invention should have a desirable viscosity level so as to create optimum protectant films. Generally, the viscosity should be at a level of from about 50–2000 cPs, more preferably from about 100–1500 cPs. As indicated previously, the compositions should have a drying time at about 72° F. ambient temperature of up to about 20 minutes and more preferably up to about 10 minutes.

The composition is used in the manner of typical teat dip products, i.e., the bovine teats are dipped into liquid compositions in order to create the long-lasting protectant films of the invention.

However, if desired, the compositions hereof can be applied by other means, such as by wiping or spraying so as to create elastic films which are vapor permeable, water-, wind-, dirt-, insect-proof and present a barrier to bacteria. The film protects the skin from damage or exposure during the healing process (in the case of wound treatments) or entrance of mastitis-causing bacteria when used as a teat dip.

DETAILED DESCRIPTION OF THE PREFERRED EMBODIMENT

The following examples illustrate preferred film protectant compositions in accordance with the invention, and demonstrate the long-lasting nature of the elastic films using such compositions. It is to be understood however, that the examples are provided by way of illustration only, and nothing therein should be taken as a limitation upon the overall scope of the invention.

EXAMPLES

The following compositions (Table 1) were prepared and tested for adherence on cow teats. In each case, the compositions were prepared by dissolving the polyether polyurethane/benzoin gum film-forming component in the THF and ethanol solvent system with subsequent addition of the nitrocellulose and other ingredients. The mixing was carried out and at ambient conditions.

TABLE 1

| Ingredient | A | B | C | D | E |
|---|---|---|---|---|---|
| Estane 5714 (polyetherpolyurethane) | 10.70 | 10.70 | 11.20 | 10.70 | 10.17 |
| Benzoin gum | 4.30 | 4.30 | 4.50 | 4.70 | 4.08 |
| THF | 79.90 | 57.93 | 57.23 | 57.53 | 51.89 |
| Ethanol | 5.00 | 26.50 | 26.50 | 26.50 | 18.29 |
| D&C Red 28 | .10 | 0.07 | 0.07 | 0.07 | 0.07 |
| 9.1% by wt. Nitrocellulose in ether | — | — | — | — | 15.00 |
| Chlorhexidine diacetate | — | 0.50 | 0.50 | 0.50 | 0.05 |

In the first adherence trial, mid-dry period cows were initially dipped with a commercially available iodine-based teat dip (Quarter Mate sold by West Agro, Inc.) To clean the cows' teats. The teats were then wiped dry and dipped with the test teat protectant composition of Table 1. All four teats of each cow were dipped with a different product. Adherence was evaluated every 24 hours. Positive adherence was determined if the teat sealant still covered the teat orifice. The results shown below confirm the incorporation of the nitrocellulose improved the adherence of the sealant.

TABLE 2

| | | % Positive Adherence | | | | | |
|---|---|---|---|---|---|---|---|
| Composition | # Cows | Day 0 | Day 1 | Day 2 | Day 3 | Day 4 | Day 5 |
| A | 12 | 100 | 100 | 100 | 96 | 72 | 43 |
| C | 12 | 100 | 100 | 100 | 91.7 | 79.2 | 56.3 |
| D | 12 | 100 | 100 | 100 | 97.9 | 89.4 | 72.3 |
| E | 12 | 100 | 100 | 97.8 | 91.3 | 84.8 | 80.4 |

In a second trial using cows that were being dried off, the teats of 21 cows were treated as described above. The adherence results shown below further confirm that the nitrocellulose-supplemented composition had much better adherence characteristics.

TABLE 3

| | | % Positive Adherence | | | | | | |
|---|---|---|---|---|---|---|---|---|
| Composition | # cows | Day 0 | Day 1 | Day 2 | Day 3 | Day 4 | Day 5 | Day 6 |
| A | 21 | 100 | 97.5 | 76.5 | 60.5 | 44.4 | 30.9 | 21.0 |
| B | 21 | 100 | 96.4 | 74.7 | 56.6 | 38.0 | 17.7 | 15.2 |
| E | 22 | 100 | 96.6 | 88.5 | 71.3 | 56.3 | 35.6 | 27.6 |

In a third trial comprising compositions A, B and E, the teats of 12 non-lactating cows were dipped in an iodine-based dip, dried thoroughly and then dipped in the test compositions. The four test compositions were used in a complete randomized design within and across the cows. Film persistence or teat end protection was evaluated every 12 hours. Composition A was used on two teats of each cow.

TABLE 4

| | Composition | | | |
|---|---|---|---|---|
| | Retention Time[1] (hrs) | | | |
| Cow | A | B | E | A |
| 1 | 60 | 60 | 84 | 60 |
| 2[2] | 108 | 108 | 108 | 108 |
| 3 | 48 | 84 | 84 | 60 |
| 4 | 60 | 84 | 132 | 120 |
| 5 | 84 | 36 | 84 | 120 |
| 6 | 60 | 132 | 84 | 60 |
| 7 | 60 | 72 | 108 | 84 |
| 8 | 84 | 84 | 132 | 60 |
| 9 | 84 | 84 | 60 | 96 |
| 10 | 24 | 36 | 72 | 36 |
| 11 | 48 | 36 | 48 | 48 |
| 12 | 48 | 72 | 132 | 60 |
| Mean Retention Time[1] | 64 | 74 | 94 | 76 |
| Range Retention Time[1] | 24–108 | 36–132 | 48–132 | 36–120 |
| # ≥ 48 hrs | 11 | 9 | 12 | 11 |
| # ≥ 72 hrs | 4 | 8 | 10 | 5 |
| # ≥ 100 hrs | 1 | 2 | 5 | 3 |

[1]Retention time-when teat ends were last seen visually covered with test composition.
[2]Dip peeled off due to milk sampling needed for another trial.

The nitrocellulose-supplemented composition E gave the best results. It had the highest (or tied for highest) on 9/12 cows and had the highest percentage of teats protected at 48, 72 and 100 hours.

The compositions F and G were prepared as described previously and compared with composition A of Table 1.

TABLE 5

| Ingredient | F | G |
|---|---|---|
| THF | 78.71 | 57.21 |
| Estane 5714 (polyether polyurethane) | 10.17 | 10.17 |
| Benzoin gum | 4.08 | 4.08 |
| D&C Red 28 | 0.1 | 0.1 |
| Ethanol | 5.00 | 26.5 |
| Nitrocellulose, 70% (ParCell R-15) | 1.94 | 1.94 |
| Viscosity @ 24° C. (60 rpm, spindle 3) | 324 cP | 330 cP |

The following Table 6 sets forth the results of the comparison between compositions F and G of Table 5 and compositions A of Table 1.

TABLE 6

| | Retention Time[1] of Test Compositions (hrs.) | | | |
|---|---|---|---|---|
| Cow # | A | F | G | A |
| 1 | 132 | 108 | 108 | 144 |
| 2 | 120 | 108 | 108 | 132 |
| 3 | 84 | 72 | 64 | 108 |
| 4 | 84 | 204 | 156 | 72 |
| 5 | 36 | 48 | 64 | 48 |
| 6 | 64 | 108 | 84 | 84 |
| 7 | 132 | 108 | 156 | 132 |
| 8 | 72 | 120 | 84 | 64 |
| 9 | 120 | 48 | 84 | 24 |
| 10 | 72 | 132 | 64 | 108 |
| 11 | 64 | 108 | 64 | 48 |
| 12 | 48 | 84 | 24 | 48 |
| Average Retention Time | 86 | 104 | 88 | 84 |
| Range | 36–132 | 48–204 | 24–156 | 24–144 |
| # of cows with greatest adherence | 1 | 6 | 2 | 3 |

[1]The compositions were tested by dipping one teat of each cow with the respective test composition. The retention time was measured at 12 hour intervals until the composition no longer effectively covered the teat duct.

The compositions in Table 7 were prepared as described above. The samples contain different ratios of the polyether polyurethane, benzoin and nitrocellulose. The total solids was adjusted to give a viscosity of a 298 to 334 cps. The adherence of the formulations were tested on 31 dry cows at the University of Guelph research herd. Products H–K were randomly applied to the four teats of one set of cows. Samples L–O were tested on a second set of cows. Adherence was determined for each product on each teat. Average retention is reported in Table 7. Because of the large cow to cow variation in adherence the number of times a product had the highest adherence is also reported. In the H–K group, product H gave the best adherence. In the L–O group, M, N and O were similar and were better than sample L.

TABLE 7

| Trial Designation | H | I | J | K | L | M | N | O |
|---|---|---|---|---|---|---|---|---|
| THF | 76.60 | 75.48 | 74.87 | 77.52 | 76.55 | 78.42 | 77.86 | 77.12 |
| Estane | 10.35 | 10.39 | 10.26 | 10.95 | 10.56 | 11.15 | 11.06 | 11.08 |
| Benzoin resinoid | 6.21 | 7.28 | 8.21 | 5.05 | 6.50 | 4.18 | 4.84 | 5.54 |
| Nitrocellulose, 70% (R-15 sec) | 1.48 | 1.48 | 1.47 | 1.20 | 1.16 | 1.00 | 0.99 | 0.99 |
| Ethanol | 5.26 | 5.27 | 5.09 | 5.18 | 5.13 | 5.15 | 5.16 | 5.17 |
| D & C Red 28 | 0.10 | 0.10 | 0.10 | 0.10 | 0.10 | 0.10 | 0.10 | 0.10 |
| Viscosity, cps (spindle 3, 60 rpm) | 310 | 318 | 318 | 330 | 298 | 312 | 322 | 334 |
| Average retention time (days) | 7.25 | 5.69 | 6.94 | 5.56 | 4.29 | 5.00 | 4.47 | 5.33 |
| Number of wins | 6 | 1 | 1 | 2 | 0 | 3 | 5 | 4 |
| Average days over runner-up | 4.0 | 1.0 | 4.0 | 3.5 | 0.0 | 1.7 | 2.0 | 2.8 |
| Number of wins/ties | 10 | 5 | 5 | 5 | 2 | 5 | 6 | 6 |
| Average days over runner-up | 2.2 | 0.2 | 0.8 | 1.4 | 0.0 | 1.0 | 1.7 | 1.8 |

Table 8 shows seven formulations that were tested for adherence on 99 cows on five herds in Canada. The formulations were prepared as described above and contained variations in the type of nitrocellulose, type of polyurethane, and supplier of benzoin resinoid. The compositions were tested in four separate groupings of four compositions as shown in Table 9. The number of times a composition had the greatest adherence on a given cow is indicated. The control composition without nitrocellulose had the lowest number of "wins" in each of the four treatment groups. Sample Q, made with the Estane 5707 polyester polyurethane, gave less adherence than the same composition made with Estane 5714 (sample P). Table 8 shows the combined average adherence for the four trial groups. Sample U provided 1.4 days better adherence than the control samples without nitrocellulose.

Four of the samples from Table 8, A, S, T and U were also tested in a split udder design at the Iowa State University research herd. The results are shown in Table 10. All three samples with nitrocellulose had better adherence than control sample without nitrocellulose.

TABLE 8

| Trial Designation | P | Q | R | A | S | T | U |
|---|---|---|---|---|---|---|---|
| THF | 76.85 | 76.85 | 76.85 | 79.90 | 76.85 | 76.85 | 75.37 |
| Estane 5714 | 10.35 | — | 10.35 | 10.70 | 10.35 | 10.35 | 10.35 |
| Estane 5707 | — | 10.35 | — | — | — | — | — |
| Daniel Benzoin | 6.21 | 6.21 | 6.21 | 4.30 | — | 6.21 | 6.21 |
| Frutarom Benzoin | — | — | — | — | 6.21 | — | — |
| Nitrocellulose, 70% (R-15 sec) | 1.49 | 1.49 | — | — | 1.49 | — | — |
| Nitrocellulose, 70% (S-0.5 sec) | — | — | 1.49 | — | — | — | — |
| Nitrocellulose, 70% (R-0.5 sec) | — | — | — | — | — | 1.49 | — |

TABLE 8-continued

| Trial Designation | P | Q | R | A | S | T | U |
|---|---|---|---|---|---|---|---|
| Nitrocelluloses, 70% (R-20 cps) | — | — | — | — | — | — | 2.97 |
| Ethanol | 5.00 | 5.00 | 5.00 | 5.00 | 5.00 | 5.00 | 5.00 |
| D & C Red 28 | 0.10 | 0.10 | 0.10 | 0.10 | 0.10 | 0.10 | 0.10 |
| Viscosity, cps (spindle 3, 60 rpm) | 310 | 206 | 268 | 220 | 300 | 242 | 270 |
| Average minimum retention time (days) | 5.90 | 5.24 | 6.18 | 5.36 | 6.27 | 5.90 | 6.76 |

TABLE 9

| # Cows in Group | | | Avg. winning/tying margin in days | | Avg. winning margin in days | |
|---|---|---|---|---|---|---|
| 26 | P | 12 | win/ties | 1.42 | 8 wins | 2.12 |
|  | Q | 8 | wins/ties | 0.62 | 1 wins | 5 |
|  | R | 9 | wins/ties | 1.11 | 5 wins | 2 |
|  | A | 8 | wins/ties | 1.50 | 4 wins | 3 |
| 24 | P | 6 | wins/ties | 2.00 | 4 wins | 3 |
|  | S | 13 | wins/ties | 1.77 | 10 wins | 2.3 |
|  | T | 8 | wins/ties | 1.25 | 5 wins | 2 |
|  | A | 3 | wins/ties | 0.33 | 1 wins | 1 |
| 24 | Q | 3 | wins/ties | 0.00 | 0 wins | 0 |
|  | R | 9 | wins/ties | 2.00 | 7 wins | 2.57 |
|  | A | 3 | wins/ties | 1.33 | 2 wins | 2 |
|  | U | 14 | wins/ties | 2.00 | 11 wins | 2.55 |
| 25 | S | 12 | wins/ties | 0.83 | 6 wins | 1.67 |
|  | T | 8 | wins/ties | 2.00 | 5 wins | 3.2 |
|  | U | 9 | wins/ties | 0.78 | 4 wins | 1.75 |
|  | A | 7 | wins/ties | 0.86 | 3 wins | 2 |

TABLE 10

| | Retention Time[1] of Test Compositions (hrs.) | | | |
|---|---|---|---|---|
| Cow # | S | T | U | A (control) |
| 1 | 108 | 72 | 120 | 84 |
| 2 | 36 | 144 | 48 | 72 |
| 3 | 144 | 108 | 144 | 60 |
| 4 | 60 | 132 | 24 | 144 |
| 5 | 96 | 48 | 60 | 72 |
| 6 | 60 | 144 | 120 | 72 |
| 7 | 144 | 36 | 108 | 48 |
| 8 | 96 | 96 | 72 | 108 |
| 9 | 108 | 84 | 144 | 48 |
| 10 | 96 | 120 | 84 | 96 |
| 11 | 84 | 72 | 60 | 48 |
| 12 | 24 | 120 | 48 | 60 |
| 13 | 132 | 96 | 96 | 48 |
| 14 | 48 | 60 | 72 | 60 |
| 15 | 132 | 24 | 60 | 24 |
| 16 | 96 | 120 | 84 | 72 |
| Average Retention Time | 82 | 92 | 84 | 70 |
| # of cows with greatest adherence | 6 | 5 | 4 | 3 |
| % > 72 hours | 69 | 75 | 62 | 50 |
| % > 96 hours | 38 | 44 | 31 | 13 |

[1]The compositions were tested by dipping one teat of each cow with the respective test composition. The retention time was measured at 12 hour intervals until the composition no longer effectively covered the teat duct.

It will thus be seen that the compositions of the invention provide a significant degree of film protection over a substantial period of time unequaled in prior compositions of this character. It will further be apparent that a wide variety of specific ingredients can be used in the formulations of the invention and at varying usage levels. The following Table 11 sets forth approximate broad and preferred ranges for essential and preferred ingredients used in the formulations, and also sets forth critical important properties.

TABLE 11

| Ingredient/Property | Approximate Broad Range | Approximate Preferred Range |
|---|---|---|
| Essential Ingredients (% by weight) | | |
| Film-forming component | 5–50 | 7–25 |
| Nitrocellulose | 0.2–15 | 1–10 |
| Carrier | qs | qs |
| Preferred Ingredients (% by weight) | | |
| Polyether polyurethane | 5–25 | 5–15 |
| Benzoin gum | 2–20 | 2–10 |
| THF | qs | qs |
| Germicide | 0.01–2 | 0.05–1 |
| Dye | 0.001–0.5 | 0.005–0.2 |
| Alcohol | 0.1–30 | 5–20 |
| Properties | | |
| Viscosity[1] | 50–2000 cPs | 100–1500 cPs |
| Drying time | 20 minutes or less | 10 minutes or less |

[1]Brookfield viscosity @ 24° C. (60 rpm, spindle #3)

We claim:

1. In a film-forming skin protectant composition capable of forming an elastic film when applied to skin and including a film-forming component comprising a mixture of polyether polyurethane and benzoin gum dispersed in a carrier, the improvement which comprises from about 0.2–15% by weight of nitrocellulose dispersed in said composition for increasing the time of adherence of the composition to the skin, as compared with an otherwise identical composition without nitrocellulose.

2. A method of protecting bovine teats comprising the step of applying to such teats the composition of claim 1, and allowing the applied composition to dry thereon and form an elastic, teat-protecting film.

3. The composition of claim 1, said level being from about 1–10% by weight.

4. The method of claim 2, said teats being the teats of non-lactating cows.

5. The composition of claim 1, said polyether polyurethane being present at a level of from about 5–25% by weight in the composition.

6. The composition of claim 5, said level being from about 5–15% by weight.

7. The composition of claim 1, said benzoin gum being present at a level of from about 2–20% by weight in the composition.

8. The composition of claim 7, said level being from about 2–10% by weight.

9. The composition of claim 1, said carrier being a solvent for said film-forming component.

10. The composition of claim 9, said solvent selected from the group consisting of tetrahydrafuran (THF), cyclohexane, toluene, $C_1$–$C_4$ ethers, $C_1$–$C_4$ ketones and $C_1$–$C_4$ alcohols, alkylene glycols and mixtures thereof.

11. The composition of claim 1, including a germicidal agent dispersed in said carrier.

12. The composition of claim 11, said germicidal agent being present at a level of from about 0.01–2% by weight in the composition.

13. The composition of claim 12, said lever being from about 0.05–1% by weight.

14. The composition of claim 11, said germicidal agent selected from the group consisting of linear or branched chain fatty acids, polyhexamethylene biguanide, chlorhexidine diacetrate, quaternary ammonium compounds and mixtures thereof.

15. The composition of claim 14, said germicidal agent comprising chlorhexidine diacetrate.

16. The composition of claim 1, including a dye dispersed in said carrier.

17. The composition of claim 16, said dye being selected from the group consisting of red, green, orange and yellow dyes and mixtures thereof.

18. The composition of claim 16, said dye being present at a level of from about 0.001–0.5% by weight in said composition.

19. The composition of claim 18, said lever being from about 0.005–0.2% by weight.

20. The composition of claim 1, said carrier comprising amounts of THF and a $C_1$–$C_4$ alcohol.

21. The composition of claim 20, said alcohol being present at a level of from about 0.1–30% by weight, with said THF making up the balance of the composition.

22. The composition of claim 21, said level being from about 5–20% by weight.

23. The composition of claim 21, said alcohol being ethanol.

24. The composition of claim 1, said composition having a viscosity of from about 50–2000 cPs.

25. The composition of claim 24, said viscosity being from about 100–1500 cPs.

26. The composition of claim 1, said composition upon application to skin at about 72° F. ambient temperature drying over a period of time up to about 20 minutes.

27. The composition of claim 26, said time being up to 10 minutes.

* * * * *